United States Patent
Bjorkholm

[11] Patent Number: 6,069,936
[45] Date of Patent: May 30, 2000

[54] MATERIAL DISCRIMINATION USING SINGLE-ENERGY X-RAY IMAGING SYSTEM

[75] Inventor: Paul J. Bjorkholm, Newport Beach, Calif.

[73] Assignee: EG&G Astrophysics, Long Beach, Calif.

[21] Appl. No.: 08/912,056

[22] Filed: Aug. 18, 1997

[51] Int. Cl.[7] .................................................. G01N 23/08
[52] U.S. Cl. ............................................ 378/98.9; 378/53
[58] Field of Search ............................... 378/98.9, 98.11, 378/98.12, 57, 53, 51, 156, 157, 158

[56] References Cited

U.S. PATENT DOCUMENTS

| | | |
|---|---|---|
| 3,848,130 | 11/1974 | Macovski . |
| 4,029,063 | 6/1977 | Alverez et al. ..................... 378/98.9 X |
| 4,366,382 | 12/1982 | Kotowski . |
| 4,731,807 | 3/1988 | Plessis et al. . |
| 4,969,175 | 11/1990 | Nelson et al. ..................... 378/98.9 X |
| 5,044,002 | 8/1991 | Stein . |
| 5,060,249 | 10/1991 | Eisen et al. ......................... 378/158 X |
| 5,247,561 | 9/1993 | Kotowski . |
| 5,285,489 | 2/1994 | Ohstuchi et al. .................. 378/158 X |
| 5,481,584 | 1/1996 | Tang et al. .............................. 378/98.9 |
| 5,524,133 | 6/1996 | Neale et al. . |

FOREIGN PATENT DOCUMENTS 0 358 965 A1  8/1989  European Pat. Off. .

*Primary Examiner*—David P. Porta
*Attorney, Agent, or Firm*—Blakely, Sokoloff, Taylor & Zafman LLP

[57] ABSTRACT

The present invention discloses a method for determining an atomic number of a location on a material using a radiation at a predetermined energy. The method comprises the steps of (i) generating the radiation at a first spectrum and a second spectrum penetrating through the location on the material; (ii) detecting a first profile corresponding to the first spectrum and a second profile corresponding to the second spectrum; and (iii) determining the atomic number of the material at the location based on the first profile and the second profile.

20 Claims, 3 Drawing Sheets

MATERIAL DISCRIMINATION USING SINGLE-ENERGY X-RAY IMAGING SYSTEM

BACKGROUND OF THE INVENTION

1. Field of the Invention

The present invention relates to the field of x-ray imaging system. In particular, the invention relates to the use of photon spectra for material discrimination in a single energy x-ray imaging system.

2. Description of Related Art

Material discrimination using x-ray radiation in a number of applications. One example of an x-ray imaging system for material discrimination is the inspection of cargo held in containers to detect target materials such as contraband drugs, illegal weapons, and explosives. To date this has not been demonstrated in practice.

There are a number of prior art techniques that are relevant to material discrimination in cargo inspection.

One technique uses dual energies at low energy. This technique relies on the difference in the photoelectric absorption and Compton scattering as a function of energy and atomic number of the material of interest. This technique is useful in airport security screening but cannot be extended to high energies which are required for cargo scanning.

Another technique is to use single high energy x rays. The high energy spectrum is detected without determining the spectral hardness. This technique merely produces a shadowgraph without characterizing the type of materials causing the shadows.

Another technique, described in U.S. Pat. No. 5,524,133, uses a number of detector configurations to determine the spectral hardness of the beam and from that infer the atomic number of the material that attenuated the beam. This technique is costly requiring extensive detector set-up.

Accordingly, there is a need in the material discrimination technology to have a single-energy x-ray imaging system that is low cost, convenient, and provides fast processing time.

SUMMARY OF THE INVENTION

The present invention discloses a method for determining an atomic number of a location in a material using radiation at a predetermined energy. The method comprises the steps of (i) generating the radiation at a first spectrum and a second spectrum penetrating through the location on the material; (ii) detecting a first profile corresponding to the first spectrum and a second profile corresponding to the second spectrum; and (iii) determining the atomic number of the material at the location based on the first profile and the second profile.

BRIEF DESCRIPTION OF THE DRAWINGS

The advantages of the present invention will become more readily apparent to those ordinarily skilled in the art after reviewing the following detailed description and accompanying drawings, wherein.

DETAILED DESCRIPTION OF THE INVENTION

The present invention discloses a single energy x-ray imaging system for material discrimination utilizing different photon energy spectra. Two images are obtained at different energy spectra for the same location. These two images are then combined to provide the average line-of-sight atomic number of the cargo. The single energy system with different energy spectra provides accurate and efficient measurement of atomic numbers of the materials.

In the following description, for purposes of explanation, numerous details are set forth in order to provide a thorough understanding of the present invention. However, it will be apparent to one skilled in the art that these specific details are not required in order to practice the present invention. In other instances, well known electrical structures and circuits are shown in block diagram form in order not to obscure the present invention unnecessarily.

Figure 1:
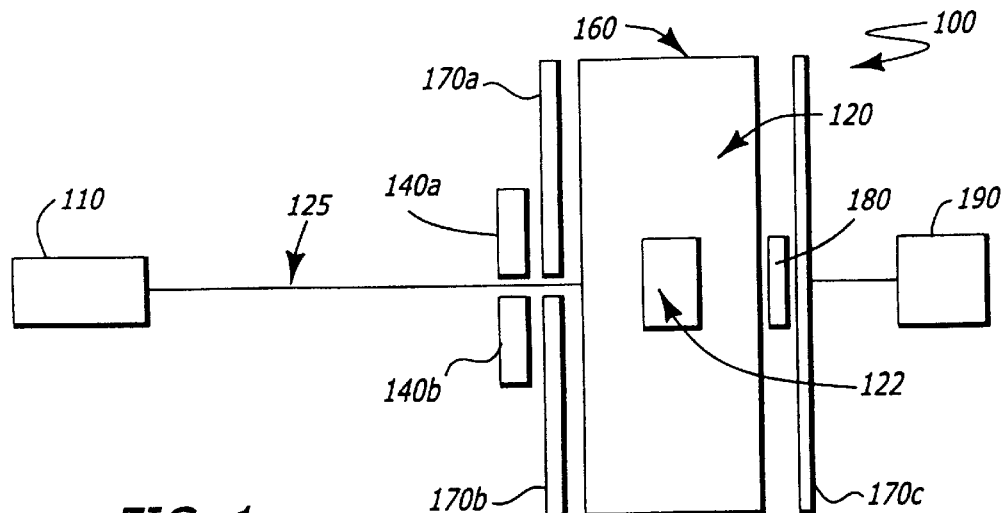
FIG. 1 is a diagram illustrating the overall of one embodiment of a system utilizing the teaching of the present invention.

Referring to FIG. 1, an illustration of one embodiment of an x-ray imaging system 100 for cargo inspection utilizing the teaching of the present invention is shown. System 100 consists of an x-ray assembly 110, an x-ray beam 125, collimator components 140a and 140b, a truck 120, a container 122, a tunnel 160, tunnel guides 170a–c, a detector 180 and a processing unit 190.

The x-ray assembly 110 provides x rays having a high energy in the order of 1 MeV–10 MeV. The x-ray beam 125 is emitted from the x-ray assembly 110 on the line-of-sight directly impinging on the object to be inspected. Collimator components 140a and 140b help define the x-ray beam. The truck 120 carries the cargo containing the material to be inspected. The truck 120 passes through the beam at a speed slow enough for the scanning of the entire image. The container 122 contains the materials to be inspected. The tunnel 160 and tunnel guides 170a–c define the scanning area for the truck 120. The detector 180 is located to receive the x-ray beam passing through the material.

The detector 180 consists of scintillating crystal elements responsive to the high energy x-ray photons and photodiode arrays to convert the light photons to electrical quantities. The detector 180 generates attenuation profiles for each scan line. The processing unit 190 receives the attenuation profiles, reconstructs the entire image of the material and processes the data to determine the atomic numbers of the scanned materials.

Figure 2:
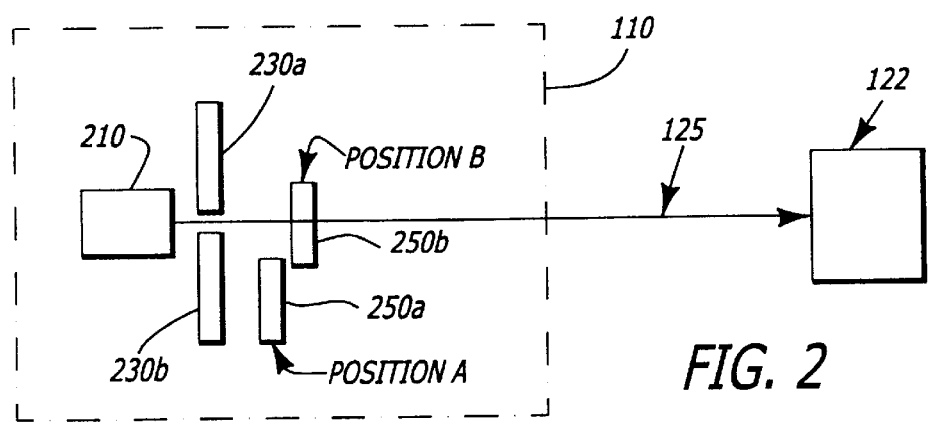
FIG. 2 is a diagram illustrating one embodiment of the present invention using external filter at the x-ray source.

Referring to FIG. 2, a diagram illustrating one embodiment of the x-ray assembly 110 in accordance to the invention is shown.

The x-ray assembly 110 consists of an x-ray source 210, collimator components 230a and 230b, and filter 250.

The x-ray source 210 provides high energy x rays. The energy is typically in the range of 1 MeV to 10 MeV. Collimator components 230a and 230b form the x rays from the x-ray source 210 into a fan beam on the line-of-sight 125 to strike the container 122. The filter 250 is used to provide at least two photon spectra for determination of the atomic number of the materials inside the container 122.

In this embodiment, the filter 250 has two positions: position A and position B. When the filter 250 is at position A, the x-ray beam goes directly to the target container 122 without going through the filter 250. The detector 180 obtains the attenuation profile of the x-ray beam as it penetrates the target materials inside the container 122 without the filter 250 at a line on the material. When the filter 250 is at position B, the x-ray beam goes through the filter 250 before striking the target container 122. The filter 250 absorbs some amount of the photon energy such that the attenuation profile as obtained by the detector 180 is modified according to the energy spectrum as filtered by the filter 250.

Therefore, at each scan line, there are two attenuation profiles corresponding to two energy spectra: one without filter and one with filter. These two attenuation profiles also correspond to the same location in the material.

The process is then repeated as the container moves through the tunnel. In the end, there are two images as reconstructed from the attenuation profiles. Both images correspond to exactly the same location on the material, one without filter (when filter 250 is at position A) and one with filter (when filter 250 is at position B).

The material for filter 250 is selected such that it modifies the original energy spectrum such that is relevant to the atomic number of the material to be discriminated. Either a low atomic number or a high atomic number material can be used as the filter material. As a guideline, a low atomic number of less than 14 or a high atomic number of greater than 46 is acceptable. A low atomic number material will harden the x-ray beam by absorbing the low energy photons and transmitting mostly high energy photons to the material under inspection. A high atomic number material will soften the x-ray beam by absorbing the high energy photons and transmitting mostly low energy photons to the material under inspection. In either case, the effect is essentially the same.

Figure 3:
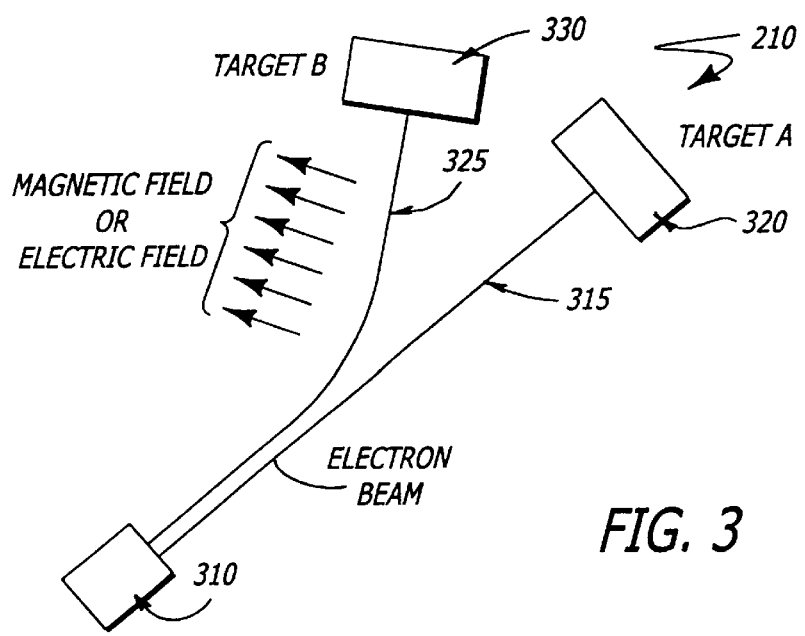
FIG. 3 is a diagram illustrating one embodiment of the present invention using different internal targets.

Referring to FIG. 3, a diagram illustrating another embodiment of the x-ray source 210 in accordance with the teaching of the present invention is shown. This embodiment does not utilize an external filter. Rather it provides different energy spectra by using different targets inside the x-ray source. The x-ray source 210 consists of an accelerator 310, target A 320, and target B 330.

Accelerator 310 produces an electron beam to bombard target A 320 along the path 315. The resulting x-ray beam exhibits an energy spectrum corresponding to the material of target A. This x-ray beam then goes through the material to be inspected. An attenuation profile is then detected for the scan line. Thereafter, the electron beam produced by accelerator 310 is deflected to bombard target B 330 along the path 325. The deflection of the electron beam can be effectuated by using the magnetic field from one target material to another, or an electric field which can be internally generated. The resulting x-ray beam exhibits an energy spectrum corresponding to the material of target B. This x-ray beam then goes through the same location of the material to be inspected. An attenuation profile representing the energy spectrum caused by target B is then detected for the scan line. The process is then repeated until two images for two energy spectra are obtained.

In an alternate embodiment, two different targets can be mechanically oscillated in front of a stationary electron beam.

The objective of this embodiment is to use different target materials to generate the x rays because the material used for the target strongly influences the shape of the x-ray energy spectrum. Thus, the targets act like internal filters to produce the x rays at different energy spectra.

The material for the two targets should be carefully selected. They should have high thermal capacity. One target should be of material having a high atomic number such as tungsten. The other target should be of material having a moderately high atomic number such as barium, bismuth, or even iron. The criteria for selection include the trade-off between the high discrimination capability and the efficiency of x-ray generation.

Figure 4:
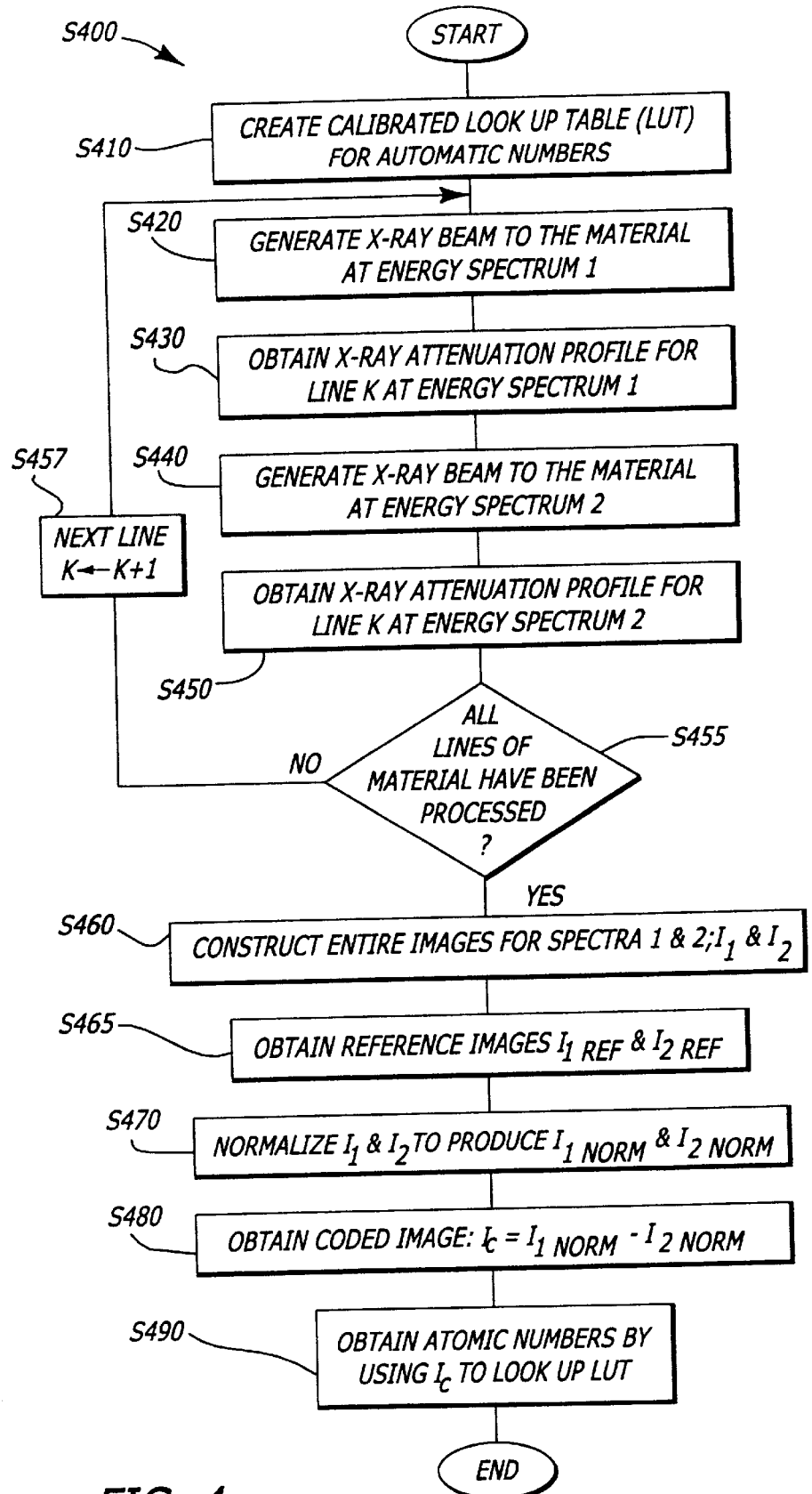
FIG. 4 is a flowchart illustrating an overall process to determine the average atomic numbers in accordance to the teaching of the present invention.

Referring to FIG. 4, a flow chart illustrating a process S400 to determine the average atomic numbers of the material in accordance to the teaching of the present invention is shown.

At start, the process S400 enters step S410. In step S410, the look up table (LUT) for the atomic numbers of the material is created. This LUT is based on a calibration procedure in which materials with known atomic numbers are subject to the operating conditions similar to the set-up described above. The LUT provides the atomic numbers as function of the indices determined by comparing the normalized images obtained at two different energy spectra. Interpolation is performed to obtain values between calibration points. This LUT is normally computed off-line during calibration.

Process S400 then proceeds to step S420. In step S420, the x-ray beam is generated to strike the material under inspection at energy spectrum 1. This energy spectrum is obtained in one of the embodiments described above. In the external filter embodiment, the energy spectrum 1 may correspond to the x-ray beam without filter. In the internal target embodiment, the energy spectrum 1 may correspond to the bombardment of the electrons on the target 1.

In step S430, the x-ray attenuation profile as provided by the detector for the line k as the result of the penetration of the x-ray beam through the material in step S420 is obtained. This attenuation profile represents the line scan for the energy spectrum 1.

Process S400 then proceeds to step S440. In step S440, the x-ray beam is generated to strike the material at the same line location (line k) at energy spectrum 2. This energy spectrum is obtained in one of the embodiments described above. In the external filter embodiment, the energy spectrum 2 may correspond to the x-ray beam with filter. In the internal target embodiment, the energy spectrum 2 may correspond to the bombardment of the electrons on the target 2.

Next, in step S450, the x-ray attenuation profile as provided by the detector for the line k as the result of the penetration of the x-ray beam through the material in step S440 is obtained. This attenuation profile represents the line scan for the energy spectrum 2.

Process S400 then proceeds to the decision step S455. In this step, it is determined if all lines of the material have been processed. In other words, it is determined if the entire material has been examined. If not, the next scan line is proceeded in step S457, i.e., the material is moved through the scanning area. Then, process S400 returns back to step S420 to repeat the same steps S420, S430, S440 and S450. If the entire material has been processed, process S400 proceeds to step S460 to begin the determination of the average atomic numbers of the material.

In step S460, the entire images of the material for energy spectra 1 and 2 are reconstructed based on the attenuation profiles of the scan lines. These images are denoted $I_1$ and $I_2$ to correspond to energy spectra 1 and 2, respectively.

In step S465, the reference images for energy spectra 1 and 2 are reconstructed based on the attenuation profiles of the scan lines. These reference images are obtained in a similar manner as described in steps S420, S430, S440 and S450 except that there is no material being interposed between the x-ray source and the detector. The reference images $I_{1REF}$ and $I_{2REF}$, therefore, correspond to the image profile of the environment in the inspection area. In most cases, this environment merely consists of air.

Process S400 then proceeds to step S470. In step S470, the two images $I_1$ and $I_2$ are normalized by eliminating the bias component caused by the reference images. One simple way to perform this normalization is to divide $I_1$ and $I_2$ by $I_{1REF}$ and $I_{2REF}$ respectively.

Process S400 then proceeds to step S480 to obtain the coded image $I_C$ containing the indices for the atomic numbers at all the locations of the material. One simple way to perform this operation is to subtract $I_{2NORM}$ from $I_{1NORM}$. As is known by one skilled in the art, it is also possible to apply other arithmetic operations on $I_{1NORM}$ and $I_{2NORM}$ to produce $I_C$. As long as this operation is consistent with the operation performed in constructing the LUT in step S410, the same result is obtained. Criteria to decide on what operation to be used include the range of the indices, the positiveness of the results, the overflow/underflow arithmetics, and the dynamic range of the atomic numbers. Conceptually, the following operations are possible:

$I_C = |I_{1NORM} - I_{2NORM}|$ were $|\cdot|$ denotes the absolute value.

$I_C = \alpha I_{1NORM} + \beta I_{2NORM}$ where $\alpha, \beta$ are two scale constant.

$I_C = \alpha \dfrac{I_{1NORM}}{I_{2NORM}}$ where $\alpha$ is a scale constant.

Finally, process S400 proceeds to step S490 to obtain the corresponding atomic numbers of the material. In this step, the individual values of the coded image $I_C$ are looked up by the LUT created at step S410 to produce the corresponding atomic numbers. The process S400 is then terminated.

Figure 5:
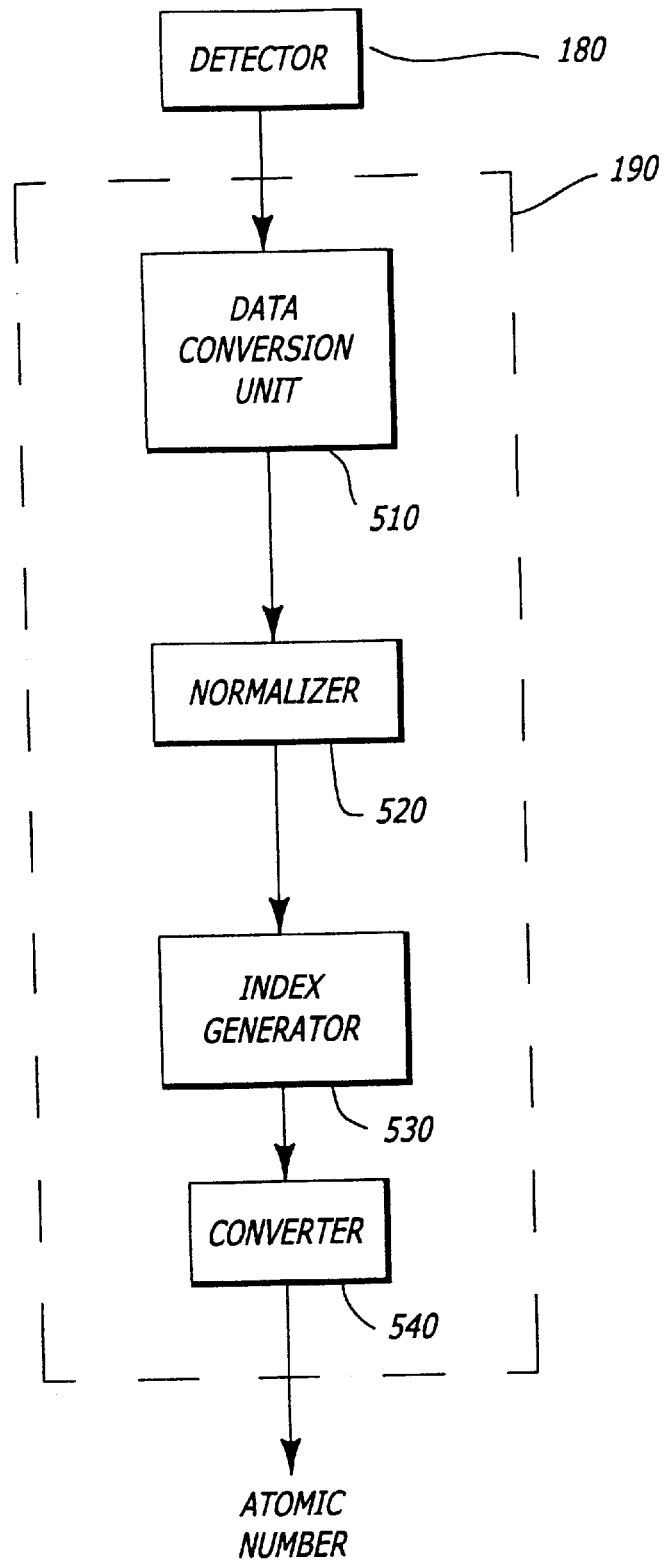
FIG. 5 is a diagram illustrating one embodiment of a processing unit in accordance to the teaching of the present invention.

Referring to FIG. 5, a diagram illustrating one embodiment of the processing unit 190 is shown. The processing unit 190 comprises a data conversion unit 510, a normalizer 520, an index generator 530 and a converter 540.

The data conversion unit 510 is coupled to the detector 180 to receive the analog quantities representing the radiation profiles. The data conversion unit 510 may consist of a signal condition circuit, a multiplexer, and an analog-to-digital converter. The signal conditioning circuit conditions, amplifies, and filters the analog signal. The multiplexer multiplexes the analog signals from the photodiodes in the detector 180. The analog-to-digital converter converts the analog signal into a digital value representing the attenuation profile.

The normalizer 520 receives the digital values from the data conversion unit 510 representing the profiles at the two energy spectra. The normalizer 520 performs the normalization process for the value of the first spectrum and the value of the second spectrum in accordance to the method described above.

The index generator 530 generates the index corresponding to the difference between the two normalized values produced by the normalizer. The converter 540 converts this index to the average atomic number of the material at the location. The converter 540 can be simply a look up table (LUT) containing predetermined atomic numbers during a calibration process as described above.

Alternatively, the processing unit 190 may consist of the data conversion unit 510 and a processor that execute a program having functional modules similar to the normalizer 520, the index generator 530, and the converter 540. The processor may process the data on a real-time basis as the attenuation profile is generated line-by-line, or when the entire image of the material is reconstructed.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for determining an atomic number of a location on a material using a radiation at a predetermined hiqh energy, the method comprising the steps of:

generating the radiation at a first spectrum and a second spectrum, at least one of the first and second spectra being obtained without filtering, the radiation penetrating without reflection through the location on the material;

detecting a first profile and a second profile, the first profile corresponding to the first spectrum, the second profile corresponding to the second spectrum; and determining the atomic number of the material at said location based on the first profile and the second profile.

2. The method of claim 1 wherein the step of determining the atomic number comprises the steps of:

normalizing the first profile and the second profile to produce the first normalized profile and the second normalized profile;

generating an index representative of a difference between the first normalized profile and the second normalized profile; and converting the index to the atomic number.

3. The method of claim 2 wherein the step of converting includes a step of looking up the atomic number in a lookup table.

4. The method of claim 3 wherein the lookup table is created by obtaining a known set of atomic numbers based on a corresponding set of materials.

5. The method of claim 2 wherein the step of normalizing includes the steps of:

detecting a first reference profile and a second reference profile, the first reference profile corresponding to the radiation at the first spectrum without the material, the second reference profile corresponding to the radiation at the second spectrum without the material; and comparing the first profile and the first reference profile, and the second profile and the second reference profile to produce the first normalized profile and the second normalized profile.

6. The method of claim 1 wherein said predetermined hiqh energy is in a range from 1 MeV to 10 MeV.

7. The method of claim 1 wherein the radiation at the first spectrum is generated without a filter.

8. The method of claim 1 wherein the radiation at the second spectrum is generated with a filter.

9. The method of claim 8 wherein said filter is made of a material having a low atomic number.

10. The method of claim 8 wherein said filter is made of a material having a high atomic number.

11. The method of claim 1 wherein the radiation at the first spectrum is generated by bombarding an electron beam onto a first target, said first target having a first atomic number.

12. The method of claim 11 wherein the radiation at the second spectrum is generated by bombarding the electron beam onto a second target, said second target having a second atomic number.

13. A system for determining an atomic number at a location of a material using a radiation at a predetermined high energy, the system comprising:

a radiation generator to generate the radiation at a first spectrum and a second spectrum, at least one of the first and second spectra being obtained without filtering;

a detector located to receive the radiation at the first spectrum and the second spectrum penetrating without reflection through the location of the material, the detector producing a first profile and a second profile, the first profile corresponding to the first spectrum, the second profile corresponding to the second spectrum; and a processing unit, coupled to receive the first profile and the second profile, to determine the atomic number of the material at said location based on the 24 at said location based on the first profile and the second profile.

14. The system of claim 13 wherein the processing unit comprises:

a data converter to convert the first profile to a first value and the second profile to a second value, and the first reference profile to a first reference value and the second reference profile to a second reference value;

a normalizer to produce the first normalized value and the second normalized value, the first normalized value corresponding to a comparison between the first value and the first reference value, the second normalized value corresponding to a comparison between the second value and the second reference value;

an index generator coupled to said normalizer to generate an index representative of a difference between the first normalized value and the second normalized value; and a converter coupled to said index generator to convert the index to the atomic number.

15. The system of claim 14 wherein the converter includes a look up table (LUT).

16. The system of claim 15 wherein the LUT is created by obtaining a known set of atomic numbers on a corresponding set of materials.

17. The system of claim 13 wherein said predetermined high energy is in a range from 1 MeV to 10 MeV.

18. A processing unit for determining an atomic number at a location of a material based on a first profile and a first reference profile corresponding to a first radiation at a first spectrum and a second profile and a second reference profile corresponding to a second radiation at a second spectrum, at least one of the first and second spectra being obtained without filtering, the first and second radiation penetrating without reflection through the location of the material at a predetermined hiqh energy, the processing unit comprising:

a data converter to convert the first profile to a first value and the second profile to a second value, and the first reference profile to a first reference value and the second reference profile to a second reference value;

a normalizer to produce a first normalized value and a second normalized value, the first normalized value corresponding to a comparison between the first value and the first reference value, the second normalized value corresponding to a comparison between the second value and the second reference value;

an index generator coupled to said normalizer to generate an index representative of a difference between the first normalized value and the second normalized value; and a converter coupled to said index generator to convert the index to the atomic number.

19. The processing unit of claim 18 wherein the converter includes a look up table (LUT).

20. The processing unit of claim 19 wherein the LUT is created by obtaining a known set of atomic numbers on a corresponding set of materials.

* * * * *